United States Patent
Pannu et al.

(10) Patent No.: US 12,102,820 B1
(45) Date of Patent: *Oct. 1, 2024

(54) ELECTRICAL THERAPY APPLIED TO THE BRAIN WITH INCREASED EFFICACY AND/OR DECREASED UNDESIRABLE SIDE EFFECTS, AND ASSOCIATED SYSTEMS AND METHODS

(71) Applicant: Nevro Corp., Redwood City, CA (US)

(72) Inventors: Satinderpall Singh Pannu, Pleasanton, CA (US); Bradford Evan Gliner, Sammamish, WA (US)

(73) Assignee: Nevro Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/967,805

(22) Filed: Oct. 17, 2022

Related U.S. Application Data

(63) Continuation of application No. 16/127,098, filed on Sep. 10, 2018, now abandoned.

(60) Provisional application No. 62/643,128, filed on Mar. 14, 2018, provisional application No. 62/556,183, filed on Sep. 8, 2017.

(51) Int. Cl.
*A61N 1/05* (2006.01)
*A61N 1/36* (2006.01)
*A61B 5/291* (2021.01)

(52) U.S. Cl.
CPC ......... *A61N 1/0534* (2013.01); *A61N 1/0531* (2013.01); *A61N 1/36082* (2013.01); *A61B 5/291* (2021.01); *A61N 1/36064* (2013.01); *A61N 1/36171* (2013.01)

(58) Field of Classification Search
CPC .............. A61N 1/0534; A61N 1/05312; A61N 1/36082; A61N 1/36064; A61N 1/3617; A61B 5/291
See application file for complete search history.

(56) References Cited

U.S. PATENT DOCUMENTS

| | | |
|---|---|---|
| 5,683,422 A | 11/1997 | Rise |
| 5,707,396 A | 1/1998 | Benbid |
| 7,313,442 B2 | 12/2007 | Velasco et al. |
| 7,346,395 B2 | 3/2008 | Lozano et al. |

(Continued)

FOREIGN PATENT DOCUMENTS

WO     WO-2015013252     1/2015

OTHER PUBLICATIONS

U.S. Appl. No. 15/365,846, filed Nov. 30, 2016, Lee.
U.S. Appl. No. 16/127,098, filed Sep. 10, 2018, Pannu.
Akbari et al., "The proposed mechanisms of radio frequency waves (RFWs) on nervous system functions impairment," Comp Clin Patho, 2015, 13 pages.

(Continued)

*Primary Examiner* — Rex R Holmes
*Assistant Examiner* — Jennifer L Ghand
(74) *Attorney, Agent, or Firm* — Perkins Coie LLP

(57) ABSTRACT

Electrical therapy applied to the brain with increased efficacy and/or decreased undesirable side effects, and associated systems and methods, are disclosed. A representative method includes applying a therapy signal to a patient, via at least one electrode at a subdural or epidural location at the patient's brain, to provide effective therapy that reduces or eliminates the effects of a patient disorder. The therapy signal does not induce any non-therapeutic side effects, and has a frequency in a frequency range of from 1.2 kHz to 500 kHz, an amplitude in an amplitude range from 0.1 to 20 mA, and a pulse width in a pulse width range from 1 microsecond to 400 microseconds.

29 Claims, 7 Drawing Sheets

(56) References Cited

U.S. PATENT DOCUMENTS

| | | |
|---|---|---|
| 7,653,433 B2 | 1/2010 | Lozano et al. |
| 8,190,264 B2 | 5/2012 | Lozano et al. |
| 8,195,298 B2 | 6/2012 | Lozano et al. |
| 8,280,514 B2 | 10/2012 | Lozano et al. |
| 8,315,703 B2 | 11/2012 | Lozano et al. |
| 8,355,797 B2 | 1/2013 | Caparso et al. |
| 8,428,735 B2 | 4/2013 | Littlewood |
| 8,467,878 B2 | 6/2013 | Lozano et al. |
| 8,712,533 B2 | 4/2014 | Alataris et al. |
| 8,798,754 B2 | 8/2014 | Knudson et al. |
| 8,849,392 B2 | 9/2014 | Lozano et al. |
| 8,909,342 B2 | 12/2014 | Lozano et al. |
| 9,278,215 B2 | 3/2016 | Thacker et al. |
| 9,327,121 B2 | 5/2016 | Thacker et al. |
| 9,446,238 B2 | 9/2016 | Lozano et al. |
| 9,884,198 B2 | 2/2018 | Parker |
| 9,895,539 B1 | 2/2018 | Heit et al. |
| 10,493,275 B2 | 12/2019 | Alataris et al. |
| 10,751,536 B1 * | 8/2020 | Heit .................. A61N 1/36062 |
| 11,123,549 B1 | 9/2021 | Pannu |
| 11,123,565 B1 | 9/2021 | Thacker et al. |
| 11,446,504 B1 | 9/2022 | Lee |
| 2004/0111127 A1 | 6/2004 | Gliner |
| 2005/0197678 A1 | 9/2005 | Boveja |
| 2006/0004422 A1 | 1/2006 | DeRidder et al. |
| 2006/0015153 A1 | 1/2006 | Gliner |
| 2006/0155348 A1 | 7/2006 | deCharms |
| 2006/0161218 A1 | 7/2006 | Danilov |
| 2009/0054829 A1 | 2/2009 | Chen |
| 2009/0204173 A1 | 8/2009 | Fang et al. |
| 2010/0191307 A1 | 7/2010 | Fang et al. |
| 2010/0274312 A1 | 10/2010 | Alataris et al. |
| 2010/0274317 A1 | 10/2010 | Parker et al. |
| 2011/0071593 A1 | 3/2011 | Parker et al. |
| 2012/0065699 A1 | 3/2012 | Bedenbaugh |
| 2012/0172946 A1 | 7/2012 | Alataris et al. |
| 2013/0066411 A1 | 3/2013 | Thacker et al. |
| 2014/0207207 A1 | 7/2014 | Alataris et al. |
| 2014/0316497 A1 | 10/2014 | Gaunt et al. |
| 2015/0217116 A1 | 8/2015 | Parramon et al. |
| 2016/0175594 A1 | 6/2016 | Min |
| 2017/0165485 A1 | 6/2017 | Sullivan et al. |
| 2017/0216587 A1 | 8/2017 | Parker |
| 2017/0281949 A1 | 10/2017 | Thacker et al. |
| 2018/0280691 A1 | 10/2018 | Ackermann et al. |

OTHER PUBLICATIONS

Benabid et al., "Chronic electrical stimulation of the ventralis intermedius nucleus of the thalamus as a treatment of the movement disorders," Journal of Neurosurg, 1996, 12 pages.

Benabid et al., "Deep brain stimulation of the subthalamic nucleus for the treatment of Parkinson's disease," www.thelancet.com/neurology, vol. 8, Jan. 2009, 15 pages.

Benabid et al., "Long-Term suppression of tremor by chronic stimulation of the ventral intermediate," The Lancet, vol. 337, 1991, 4 pages.

Benabid et al., "Chronic Electrical Stimulation of the Ventralis Intermedius Nucleus of hte Thalamus and of Other Nuclei as a Treatment of Parkinson's Disease," Techniques in Neurosurgery, vol. 5, No. 1, 1999, 26 pages.

Cabezas et al., "The role of glial cells in Alzheimer disease: potential therapeutic implications," Neurologia, 2014, 5 pages.

Dayal et al., "Subthalamic Nucleus Deep Brain Stimulation in Parkinson's Disease: The Effect of Varying Stimulation Parameters," Journal of Parkinson's Disease 7, 2017, 11 pages.

Holm et al., "Insights into Pathology of the $\infty 3$ Na+/K+-ATPase Ion Pump in Neurological Disorders; Lessons from Animal Models," Frontier in Physiology, 2016, 12 pages.

Kann, Oliver, "The interneuron energy hypothesis: Implications for brain disease," Neurobiology of Disease, 2015, 11 pages.

Kinoshita et al., "The Influence of Na+, K+-ATPase on Glutamate Signaling in Neurodegenerative Diseases and Senescence," Frontiers in Physiology, Jun. 2016, 19 pages.

Liu et al., "Activation of Na+ and K+ Pumping Modes of Na,k)-ATPase by an Oscillating Electric Field," The Journal of Biological Chemistry, vol. 265, May 5, 1990, 9 pages.

Miller et al., "Electric Field Driven Torque in ATP Synthase," PLoS One, vol. 8, Issue 9, Sep. 2013, 9 pages.

Response to Non-Final Office Action for U.S. Appl. No. 15/798,110, filed on Mar. 5, 2021, Applicant: Nevro Corporation, 17 pages.

Steigerwald et al., "Pulse Duration Settings in Subthalamic Stimulation for Parkinson's Disease," Movement Disorders, vol. 33, No. 1, 2018, 5 pages.

Tsong, Tian Yow, "Electrical Modulation of Membrane Proteins: Enforced Conformational Oscillations and Biological Energy and Signal Transductions," Annu. Rev. Biophys. Biophys. Chem., 1990, 24 pages.

Vitvitsky et al., "Na+ and K+ ion imbalances in Alzheimer's disease," Biochimica et Biophysica Acta, Elsevier, 2012, 11 pages.

\* cited by examiner

| Indication | Target(s) | Rating Scale/Metric | Clinically Significant Improvement |
|---|---|---|---|
| *Movement Disorders* | | | |
| Parkinson's disease (PD) | - Globus pallidus internus (GPi)<br>- Subthalamic nucleus (STN) | - Unified Parkinson's Disease Rating Scale III (UPDRS-III)<br>- Parkinson's Disease Questionnaire (PDQ-39)<br>- Parkinson's Disease Quality of Life Questionnaire (PDQL)<br>- Beck Depression Inventory-II (BDI-II)<br>- Activities of Daily Living (ADL) | ≥30% reduction in UPDRS-III score |
| Essential tremor (ET) | - Ventral intermediate nucleus of the Thalamus (Vim) | - The Essential Tremor Rating Assessment Scale (TETRAS)<br>- Fahn-Tolosa-Marin Clinical Rating Scale for Tremor (FTM) | ≥40% reduction in tremor score |
| Dystonia (e.g., generalized or segmental primary dystonia; myoclonus-dystonia; secondary dystonia) | - Globus pallidus internus (GPi) | - Fahn-Marsden Scale (FM)<br>- Burke-Fahn-Marsden Dystonia Rating Scale (BFMDRS or BFM)<br>- Unified Dystonia Rating Scale (UDRS)<br>- Global Dystonia Rating Scale (GDRS)<br>- Toronto Western Spasmodic Torticollis Rating Scale (TWSTRS) | ≥40% reduction in BFMDRS severity score |
| Multiple sclerosis (MS) tremor | - Ventral intermediate nucleus of the Thalamus (Vim)<br>- Ventral oralis anterior/ventral oralis posterior nuclei of the thalamus (Voa/Vop) | - Fahn-Tolosa-Marin Clinical Rating Scale for Tremor (FTM) | ≥30% reduction in FTM score |
| *Psychiatric Indications* | | | |
| Depression (major depressive disorder [MDD]) | - Subcallosal cingulate gyrus (SCG)/(Cg25)<br>- Nucleus accumbens (NAc)<br>- Ventral capsule/ ventral striatum (VC/VS)<br>- Medial forebrain bundle (MFB)<br>- Inferior thalamic peduncle (ITP)<br>- Internal capsule/ bed nucleus of the stria terminalis (IC/BST) | - Hamilton Rating Scale for Depression (HRSD or HDRS or HAM-D)<br>- Montgomery–Åsberg Depression Rating Scale (MADRS)<br>- Beck Depression Inventory II (BDI-II) | ≥30% reduction in HRSD, MADRS, or BDI score |

*FIG. 5*

| Indication | Target(s) | Rating Scale/Metric | Clinically Significant Improvement |
|---|---|---|---|
| *Psychiatric Indications (cont.)* | | | |
| Obsessive-compulsive disorder (OCD) | - Anterior limb of internal capsule (ALIC)<br>- Nucleus accumbens (NAc)<br>- Ventral capsule/ ventral striatum (VC/VS)<br>- Inferior thalamic peduncle (ITP)<br>- Subthalamic nucleus (STN) | - Yale-Brown Obsessive-Compulsive Scale (Y-BOCS)<br>- Hamilton Anxiety Rating Scale (HARS or HAM-A)<br>- Hamilton Rating Scale for Depression (HRSD or HDRS or HAM-D)<br>- Global Assessment of Functioning (GAF) | ≥35% reduction in Y-BOCS |
| Tourette syndrome (TS) | - Midline thalamus: centromedian nucleus–parafascicular complex of the thalamus (CM-Pf)<br>- Anterior limb of internal capsule (ALIC)<br>- Nucleus accumbens (NAC)<br>- Globus pallidus internus (GPi) | - Yale Global Tic Severity Scale (YGTSS)<br>- Tourette Syndrome Symptom List (TSSL)<br>- Rush Video-based Tic Rating Scale (RVTRS) | ≥35% reduction in vocal and/or motor tics |
| Generalized anxiety disorder (GAD) | - Nucleus accumbens (NAc)<br>- Ventral capsule/ ventral striatum (VC/VS) | - Hamilton Anxiety Rating Scale (HARS or HAM-A)<br>- Beck Anxiety Inventory (BAI) | ≥35% reduction in HAM-A score |
| Anorexia nervosa (AN) | - Subcallosal cingulate gyrus (SCG)/(Cg25)<br>- Nucleus accumbens (NAc) | - Hamilton Rating Scale for Depression (HRSD or HDRS or HAM-D)<br>- Difficulties in Emotion Regulation Scale (DERS)<br>- Body mass index (BMI)<br>- Yale-Brown-Cornell Eating Disorder Scale (YBC-EDS)<br>- BAI | Significant BMI increase + concomitant HRSD/BAI/DERS score reduction |
| Addiction (e.g., alcohol, nicotine, heroin) | - Nucleus accumbens (NAc) | - Drug use frequency<br>- Drug use amount | >rate of cessation in comparison to non-DBS pts. |

*FIG. 5 (continued)*

| Indication | Target(s) | Rating Scale/Metric | Clinically Significant Improvement |
|---|---|---|---|
| *Pain Indications* | | | |
| Chronic cluster headache (CCH)<br>*Also: SUNCT/SUNA headache\** | - Posterior hypothalamus (pHyp)<br>- Ventral tegmental area (VTA)<br>- Sphenopalatine ganglion (SPG) | - Verbal rating scale (VRS)<br>- Headache load (HAL)<br>- Migraine Disability Assessment Scale (MIDAS)<br>- Categorical pain scale (CPS)<br>- Headache-specific disability score (HIT-6) | ≥30% reduction in frequency, intensity, or both, of CH attacks |
| Pain<br>(e.g., back pain (BP), failed back surgery syndrome (FBSS), phantom limb pain (PLP), post-stroke pain (PSP), spinal cord injury (SCI) | - Periventricular grey (PVG)<br>- Periaqueductal grey (PAG)<br>- Internal capsule (IC)<br>- Sensory thalamus (ST): ventral posterior medial/ ventral posterior lateral thalamic nuclei (VPM/VPL)<br>- Motor cortex stimulation (MCS) | - Visual analog scale (VAS)<br>- Numeric rating scale (NRS)<br>- Pain disability index (PDI)<br>- Percent pain relief (PPR)<br>- McGill Pain Questionnaire (MPQ) | ≥50% reduction in pain score |
| *Miscellaneous Indications* | | | |
| Epilepsy | - Caudate Nucleus (CN)<br>- Cerebellar dentate nucleus (CDN)<br>- Subthalamic nucleus (STN)<br>- Midline thalamus: centromedian nucleus–parafascicular complex of the thalamus (CM-Pf)<br>- Intralaminar nucleus of thalamus (ILN)<br>- Anterior thalamic nucleus (AN)<br>- Amygdalo-hippocampus (AH)/ medial temporal lobe (MTL) | - Seizure frequency<br>- Seizure severity | ≥50% seizure frequency reduction |
| Alzheimer's disease (AD) | - Fornix/hypothalamus<br>- Nucleus basalis of Meynert (NBM) | - The Clinical Dementia Rating (CDR)<br>- Alzheimer's disease Assessment Scale Cognitive subscale (ADAS-cog)<br>- Mini Mental Status Examination (MMSE) | Stabilized or slowed rate of cognitive decline vs control pts. |
| Post-traumatic stress disorder (PTSD) | - Amygdala<br>- Stria terminalis | - Clinician-Administered PTSD Scale (CAPS)<br>- Davidson Trauma Scale (DTS)<br>- Hamilton Anxiety Rating Scale (HARS<br>- Montgomery–Åsberg Depression Rating Scale (MADRS) | No controlled human data found |

\*Headache abbreviations: Short-lasting unilateral neuralgiform headache attacks with conjunctival injection and tearing (SUNCT); Short-lasting unilateral neuralgiform headache attacks with cranial autonomic features (SUNA)

ELECTRICAL THERAPY APPLIED TO THE BRAIN WITH INCREASED EFFICACY AND/OR DECREASED UNDESIRABLE SIDE EFFECTS, AND ASSOCIATED SYSTEMS AND METHODS

CROSS-REFERENCE TO RELATED APPLICATIONS

The present application is a continuation of U.S. patent application Ser. No. 16/127,098, filed on Sep. 10, 2018 which claims priority to pending U.S. Provisional Application 62/556,183, filed on Sep. 8, 2017, and pending U.S. Provisional Application 62/643,128, filed on Mar. 14, 2018, both of which are incorporated herein by reference.

TECHNICAL FIELD

The present disclosure is directed generally to electrical therapy applied to the brain with increased efficacy and/or decreased undesirable side effects, and associated systems and methods.

BACKGROUND

Deep brain stimulation (DBS) and cortical stimulation have been used for years to treat a variety of patient indications. In a typical DBS procedure, an electrical probe is inserted into the patient's brain and activated at a frequency generally under 1,200 Hz, and more typically at about 130 Hz. This relatively low frequency can synchronize neural firings in the brain and can reduce some of the effects of the patient's motor dysfunctions. For example, patients suffering from tremors can experience reduced symptoms as a result of the electrical stimulation. However, the stimulation can produce undesired side effects. Such effects can include unwanted sensory effects (e.g., paresthesia), unwanted motor effects (e.g., an inability to initiate movement, uncontrolled movement), disturbed speech, and/or unwanted cognitive effects (e.g., an inability to focus one's thoughts). Accordingly, there remains a need for improved therapies for motor dysfunctions and other neurological conditions and/or patient indications.

BRIEF DESCRIPTION OF THE DRAWINGS

FIG. 5 is a table identifying representative indications, target neural populations, rating scales, and improvement levels against which results obtained using techniques in accordance with the present technology may be measured.

DETAILED DESCRIPTION

The present technology is directed generally to brain modulation via electrical signals, and associated systems and methods for addressing motor dysfunctions and/or other patient indications. The electrical signals generally have higher fundamental frequencies than do typical signals applied to the brain. For example, portions of the waveform have higher fundamental frequencies, e.g., from 1.2 kHz to 500 kHz), and generally produce effective therapy with reduced or eliminated undesirable side effects. Such side effects can include unwanted motor stimulation or blocking, dyskinesia, interference with sensory functions, interference with speech, and/or interference with cognitive functions.

Specific details of embodiments of the technology are described below with reference to methods for modulating one or more neural populations (e.g., nerves or nerve populations) at target sites of a patient, and associated implantable structures for providing the modulation. Although embodiments are described below with reference to modulating particular brain structures, the modulation may in some instances be applied to other neurological structures and/or target populations of the brain, and/or other neurological tissues. Some embodiments can have configurations, components, or procedures different than those described in this section, and other embodiments may eliminate particular components or procedures. A person of ordinary skill in the relevant art, therefore, will understand that the present disclosure may include some embodiments with additional elements, and/or may include some embodiments without several of the features or elements shown and described below with reference to FIGS. 1-4B.

In general terms, some embodiments of the present technology are directed to producing a therapeutic effect that includes treating patient indications, for example, motor dysfunction, cognitive dysfunction, sensory dysfunction, speech dysfunction, neuropsychiatric dysfunction, and/or other dysfunction. Without being bound by theory, the therapeutic effect can be produced by quieting neural activity in the brain, and/or other mechanisms. It is further expected that the techniques described herein can produce more effective, more robust, less complicated, and/or otherwise more desirable results than can existing brain stimulation techniques. It is also expected that the techniques described below can produce therapeutic outcomes at least as good as those associated with traditional techniques, with reduced or eliminated side effects.

Representative Systems

Figure 1:
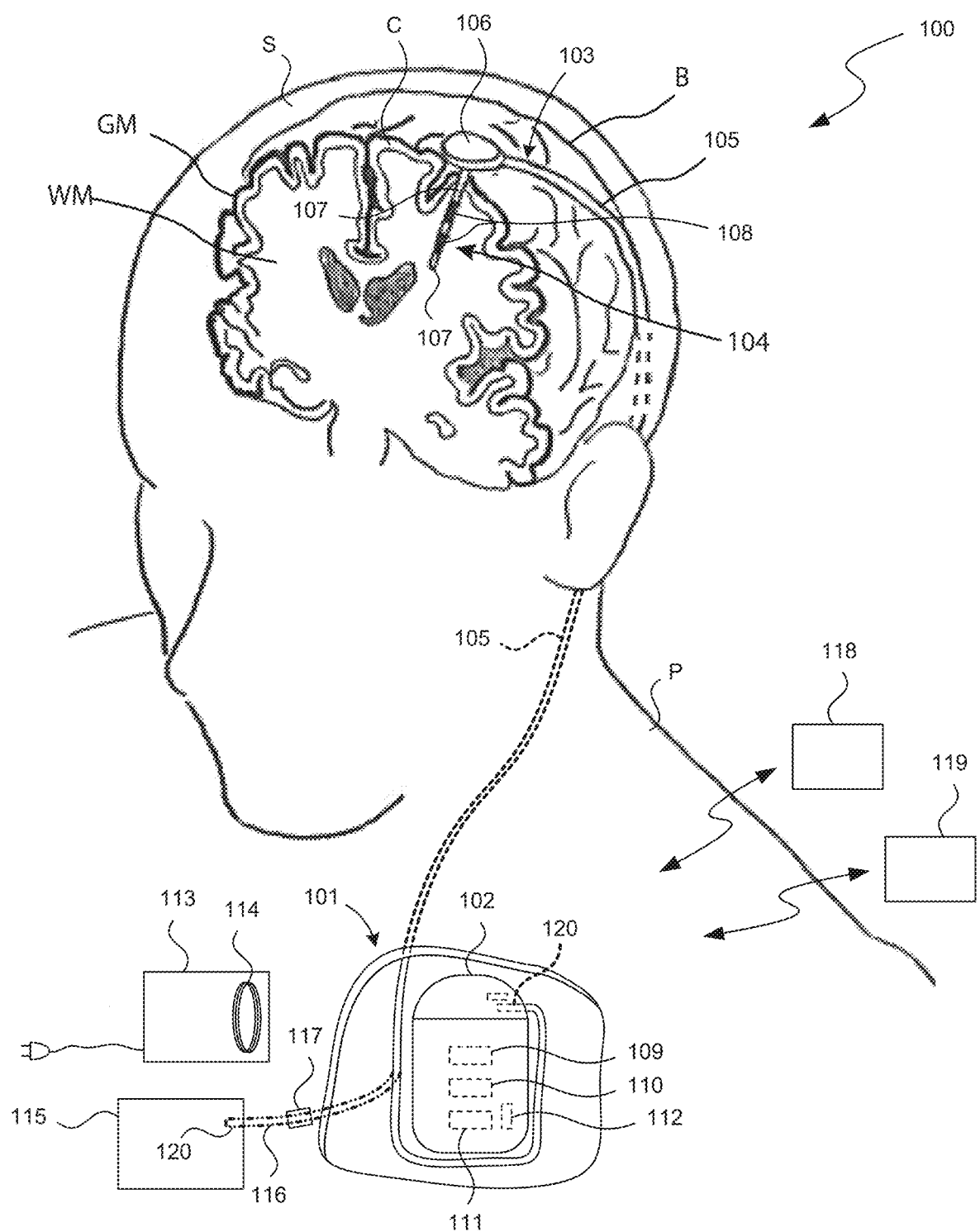
FIG. 1 is a partially schematic, partially cut-away illustration of a patient's head, illustrating a representative system configured in accordance with some embodiments of the present technology.

FIG. 1 schematically illustrates a representative treatment system 100 for treating one or more neurologic diseases (and/or other conditions) arranged relative to the general anatomy of a patient's brain B. The treatment system 100 can include a signal delivery system 101 having a signal generator 102 (e.g., a pulse generator) and a signal delivery device 103 comprising one or more signal delivery element(s) 104 (e.g., leads or probes that can include electrical signal delivery contacts). For purposes of illustration, a single signal delivery element 104 is shown in FIG. 1. The signal delivery element 104 can be positioned bilaterally (i.e., with one lead or probe in each hemisphere of the patient), or unilaterally (i.e., with both leads or probes in the same hemisphere of the patient). When the signal delivery elements 104 are positioned bilaterally, they can be implanted simultaneously or in a staged manner. The decision to deliver therapy bilaterally or unilaterally may be based on the disease or ailment being treated, and/or other factors (e.g., symptoms) of the patient. For example, in some embodiments, Parkinson's disease may be treated bilaterally (and/or unilaterally) and essential tremor disorders may be treated unilaterally (and/or bilaterally). As another example, dystonia can be treated bilaterally and/or unilaterally. The signal generator 102 can be connected or coupled to the signal delivery element(s) 104 via a signal link 105. The signal link 105 can include one or more components (e.g., one or more leads, cables, extensions and/or wireless links) between the signal delivery element(s) 104 and the signal generator 102. As shown in FIG. 1, the signal delivery element(s) 104 is configured to be positioned in or at the patient's brain B to apply an electrical signal to the brain (e.g., to the white matter WM and/or gray matter GM). The signal generator 102 may be implanted subcutaneously within the patient P, e.g., at a subclavicular location, or at another suitable location, generally near the target neural population.

The signal delivery element(s) 104 can include a head 106 connected to a probe 107, e.g., a deep brain probe. The head 106 can be positioned external to the patient's skull S, or within the patient's skull S, but external to the cortex C of the patient's brain B. The probe 107 typically extends beneath the cortex C. The probe 107 can carry one or more electrodes or contacts 108 that are electrically connected to the signal generator 102 via corresponding conductors carried by the signal link 105 (or the signal link 105 can include a wireless link). A single electrode 108 can be activated to produce a monopolar signal (with a conductive outer housing of the signal generator 102 operating as a return electrode), or multiple electrodes 108 (e.g., two, or more than two) can be activated to produce a bipolar or other multipolar signal. For example, in some embodiments, multiple electrodes 108 can be automatically selected and used to deliver therapy to a particular region between the selected electrodes. Furthermore, compared to using a single electrode 108, using multiple electrodes 108 may, in some embodiments, help conserve energy by delivering more focused energy to the particular region. Using multiple electrodes 108, compared to using a single electrode 108, can also increase efficacy and/or decrease undesirable side effects.

The signal generator 102 can transmit signals (e.g., electrical therapy signals) to the signal delivery element(s) 104 to produce a therapeutic effect on the target nerves. As used herein, and unless otherwise noted, to "modulate," "stimulate," or provide "modulation" or "stimulation" to the target nerves refers generally to producing a therapeutic effect via the electrical therapy signal. Without being bound by theory, it is believed that in at least some embodiments, the electrical therapy signals can "quiet" target neurons, without inhibiting normal neural activity by the target neurons, and/or other neurons. It is further believed, without being bound by theory, that the frequency of the signal, alone or in combination with other signal parameters, can be selected to produce the desired therapeutic effect. In at least some embodiments, other combinations of parameters may produce such effects. For example, selected pulse widths or ranges of pulse widths, can produce such effects, over a variety of frequencies and/or amplitudes.

The signal generator 102 can include a machine-readable (e.g., computer-readable) medium containing instructions for generating and transmitting suitable therapy signals. The signal generator 102 and/or other elements of the treatment system 100 can include one or more processors 109, memories 110 and/or input/output devices 111. Accordingly, the process of providing electrical signals, detecting physiological parameters of the patient, adjusting the modulation signal, and/or executing other associated functions can be performed by computer-executable instructions contained by, on, or in computer-readable media located at the signal generator 102 and/or other system components. The signal generator 102 can include multiple portions, elements, and/or subsystems (e.g., for directing signals in accordance with multiple signal delivery parameters) housed in a single housing, as shown in FIG. 1, or in multiple housings.

The signal delivery system 101 can include one or more sensing elements 112 for detecting one or more physiological parameters of the patient before, during, and/or after the application of electrical therapy signals. In some embodiments, one or more of the sensing elements 112 can be carried by the signal generator 102, the signal delivery element(s) 104, and/or other implanted components of the system 101. In some embodiments, the sensing element(s) 112 can be an extracorporeal or implantable device separate from the signal generator 102 and/or the signal delivery element(s) 104. Representative sensing elements 112 include one or more of: an accelerometer, a temperature sensor, an impedance sensor, a chemical sensor, a biosensor, an electrochemical sensor, a hemodynamic sensor, an optical sensor and/or other suitable sensing devices. Some examples of physiological parameters that can be detected by the sensing element(s) 112 include patient tremor, patient position, patient posture, patient activity level, neurotransmitter concentration, hormone concentration, local impedance, current, and/or voltage levels, and/or any correlates and/or derivatives of the foregoing parameters (e.g., raw data values, including voltages and/or other directly measured values). The foregoing parameters can reflect patient state and/or other patient-dependent variables, and/or variables that are patient-independent (e.g., time). Further details are included in U.S. Pat. No. 8,355,797, which is incorporated herein by reference in its entirety.

The signal generator 102 can receive and respond to one or more input signals received from one or more sources. The input signals can direct or influence the manner in which the therapy and/or process instructions are selected, executed, updated, and/or otherwise performed. The input signals can be received via one or more input/output devices 111 that are carried by the signal generator 102 and/or distributed outside the signal generator 102 (e.g., at other patient locations) while still communicating with the signal generator 102. In some embodiments, the input/output devices include wireless communication elements for communicating with external controllers or programmers, as described in further detail later.

In some embodiments, the signal generator 102 can obtain power to generate the therapy signals from an external power source 113. The external power source 113 can transmit power to the implanted signal generator 102 using electromagnetic induction (e.g., RF signals). For example, the external power source 113 can include an external coil 114 that communicates with a corresponding internal coil (not shown) within the implantable signal generator 102. The external power source 113 can be portable for ease of use.

In some embodiments, the signal generator 102 can obtain the power to generate therapy signals from an internal power source, in addition to or in lieu of the external power source 113. For example, the implantable signal generator 102 can include a non-rechargeable battery or a rechargeable battery to provide such power. When the internal power source includes a rechargeable battery, the external power source 113 can be used to recharge the battery. The external power source 113 can in turn be recharged from a suitable power source (e.g., conventional wall power). When the internal power source includes a non-rechargeable battery, the non-rechargeable battery can be removed from the patient and replaced after a set period of time or after receiving a low battery indication. The non-rechargeable battery arrangement may not include as many components as the rechargeable battery (e.g., may not include an inductive receiver), and thus the battery can be made larger to provide a greater battery capacity (e.g., more battery cells) and thus a longer operating lifespan.

As described above, the signal generator 102 may be implanted subcutaneously within the patient P, e.g., at a subclavicular location, or at another suitable location, generally near the target neural population. The signal delivery element(s) 104 can be implanted at a similar time (e.g., during the same procedure) and introduced into the patient's head so as to be adjacent a selected brain region. As described in further detail below, the signal delivery element(s) 104 can be intravascularly introduced or non-vascularly introduced into the patient's head through, e.g., a burr hole drilled in the patient's cranium or by performing a craniotomy. Once the signal generator 102 and signal delivery element(s) 104 are both implanted and connected or coupled to one another, a functional testing procedure (e.g., to check impedance or the connection between the signal generator 102 and signal delivery element(s) 104) may be performed.

Simply implanting the signal delivery element(s) 104 can, on its own (i.e., without any electrical stimulation), cause therapeutic effects in some patients, including, e.g., reduced undesirable movement (e.g., tremors), reduced rigidity of movement, and/or a greater ability to initiate movement. These therapeutic effects are temporary (e.g., can last approximately 2-6 weeks) and are often referred to as the "insertion effect." Accordingly, after the functional testing is complete, the practitioner may turn the signal generator 102 off until after the insertion effect has, or is expected to have, ceased.

Following the implantation procedure, the signal delivery parameters provided by the signal generator 102 can be programmed or updated from their default values. In some embodiments, programming the signal generator 102 is performed a period of time after the implantation (e.g., 6-8 weeks after implantation) to ensure any patient response to the therapeutic signals delivered via the signal delivery element(s) 104 are based on the therapeutic signal itself and not on other factors (e.g., the "insertion effect," as described above). The signal generator 102 can be programmed via a wireless physician's programmer or controller 118 (e.g., a physician's remote) and/or a wireless patient programmer or controller 119 (e.g., a patient remote). Generally, the patient P has control over fewer parameters than does the practitioner. For example, the capability of the patient programmer 119 may be limited to starting and/or stopping the signal generator 102, and/or adjusting the signal amplitude. The patient programmer 119 may be configured to accept therapy feedback information (e.g., tremor and/or other movement data) as well as other variables, such as medication use.

In addition to or in lieu of portions of the foregoing implantation procedure, the patient may undergo a trial period during which the functionality and/or the effectiveness of the therapeutic signals delivered via the signal delivery element(s) 104 are tested. For example, during the trial period, an external signal generator 115 (e.g., a trial modulator) can be coupled to the signal delivery element(s) 104. For example, a practitioner (e.g., a physician and/or a company representative) can use the external signal generator 115 to vary the modulation parameters provided to the signal delivery element(s) 104 in real time, and (a) determine if the patient responds favorably, and/or (b) select optimal or particularly efficacious parameters. These parameters can include the location from which the electrical signals are emitted, as well as the characteristics of the electrical signals provided to the signal delivery element(s) 104. In some embodiments, input collected via the external signal generator 115 can be used by the clinician to help determine which parameters to vary. In a typical process, the practitioner uses a cable assembly 116 (or a wireless link) to temporarily connect the external signal generator 115 to the signal delivery element(s) 104. The practitioner can test the efficacy of the signal delivery element(s) 104 in an initial position. The practitioner can then disconnect the cable assembly 116 (e.g., at a connector 117), reposition the signal delivery element(s) 104, and reapply the electrical signal. This process can be performed iteratively until the practitioner obtains the desired signal parameters and/or position for the signal delivery element(s) 104. Optionally, the practitioner can move the partially implanted signal delivery element(s) 104 without disconnecting the cable assembly 116. Furthermore, in some embodiments, the iterative process of repositioning the signal delivery device 103 and/or varying the therapy parameters may be eliminated.

When the signal delivery element(s) 104 is implanted, the patient P can receive therapy via signals generated and transmitted by the external signal generator 115, generally for a limited period of time (e.g., during the trial period). During this time, the patient wears the cable assembly 116 and the external signal generator 115 outside the body. Assuming the trial therapy is effective or shows the promise of being effective, the practitioner then replaces the external signal generator 115 with the implanted signal generator 102. The implanted signal generator 102 may include default programs or therapy programs selected based on the experience gained during the trial period. Optionally, the practitioner can also replace the signal delivery element(s) 104.

The implantable signal generator 102, the external signal generator 115 and/or the connector 117 can each include one or more receiving elements 120. Accordingly, the receiving elements 120 can be patient-implantable elements, or the receiving elements 120 can be integral with an external patient treatment element, device or component (e.g., the external signal generator 115 and/or the connector 117). The receiving elements 120 can be configured to facilitate a simple coupling and decoupling procedure between the signal delivery element(s) 104, the signal link 105, the pulse generator 102, the external signal generator 115 and/or the connector 117.

Representative Therapy Targets and Delivery Techniques

In some aspects of the present technology, one or more signal delivery element(s) 104 may be positioned within the patient's head, to modulate neurons at any suitable lobe or other structure of the cortex or deep brain. Examples of deep brain regions that can be modulated include, for example, the thalamus, the anterior thalamus, the ventrolateral thalamus, the internal segment of the globus pallidus (GPi), the substantia nigra pars reticulata (SNr), the subthalamic nucleus (STN), the external segment of the globus pallidus (GPe), the neostriatum, the cingulate cortex, the cingulate gyrus, and/or other regions. Other examples of deep brain regions that can be modulated include the habenula (e.g., the lateral habenula (LHb)). In some embodiments, delivering electrical signals from signal delivery element(s) adjacent or in the habenula region, or more particularly the LHb region, can cause therapeutic effects via one or more of the mechanisms of action (e.g., quieting neural activity) identified above. In some embodiments, modulation may cause certain receptors (e.g., N-methyl-D-aspartate (NMDA) receptors) to be blocked, thereby allowing other neurons to activate or fire at a relatively increased rate. In any of the foregoing embodiments, positioning the signal delivery element(s) adjacent to or in such deep brain regions and delivering an electrical therapy signal in accordance with the parameters described herein can cause therapeutic effects via quieting neural activity and/or another mechanism of action.

In some embodiments, the signal delivery element(s) may be positioned in or adjacent to cortical structures/regions, in addition to, or in lieu of, placement at deep brain structures. The cortical structures can be targeted from an epidural location and/or a subdural location. Examples of cortical structures/regions that can be modulated include the dorsolateral prefrontal cortex (e.g., to treat depression), the motor cortex (e.g., to treat movement disorders), the sensory cortex (e.g., to treat tinnitus), and/or other structures/regions, e.g., the motor strip, the sensory strip, and/or the pre-motor cortex. In some embodiments, the signal delivery element(s) 104 can be delivered to any one of a number of suitable vessels in order to place the electrodes adjacent the tissue to be stimulated, whether deep brain or cortical. Examples of veins providing access to deep brain structures include the inferior sagittal sinus, pericallosal sinus, cavernous sinus, sphenoid sinus, temporal basal vein, and occipital veins. Examples of arteries providing access to the deep brain include branches off the internal carotid or vertebral arteries. Examples of veins providing access to the cortex include the superior sagittal sinus, any of the superior cerebral veins branching from the superior sagittal sinus (e.g., the lacuna, the frontopolar vein, the anterior frontal vein, the posterior frontal vein, the precentral vein, the central vein, the anterior parietal vein, the posterior parietal vein, and the occipital vein), the superior sylvian vein, the vein of Labbe, the vein of Trolard, the inferior sagittal sinus, and any inferior cerebral veins branching off of the inferior sagittal sinus, transverse sinus, and/or meningeal sinus. Examples of arteries providing access to the cortex include any of the branches off the external carotid arteries, the maxillary arteries, and/or the meningeal arteries. The vascular approach for introducing a signal delivery device can allow the practitioner to reach more cortical structures, especially in the folds of the cortex, than can be reached via cortical stimulation applied epidurally or subdurally. While the blood vessels are smaller in the deep brain structures, this approach can also increase the possible target structures for deep brain stimulation, as described above.

In embodiments for which the signal delivery element(s) 104 are introduced intravascularly, the jugular and/or femoral veins can be used as intravascular access points from which the signal delivery element(s) 104 can be delivered to the above-described veins, and the carotid and/or femoral arteries can be used as intravascular access points from which the signal delivery element(s) 104 can be delivered to the above-described arteries.

To access those brain regions that are not adjacent to easily-accessible or navigable blood vessels, the treatment site may be accessed by non-vascular techniques, e.g., via a burr hole drilled in the patient's cranium, or by performing a craniotomy. The technique can further include penetrating the parenchyma for deep brain stimulation (as shown in FIG. 1), or by epidurally or subdurally placing the signal delivery element(s) 104 along the cortex for cortical stimulation (as described further below with reference to FIG. 2). Thus, it will be appreciated that intravascular and/or non-vascular placement techniques for the signal delivery element(s) 104 can be utilized in procedures involving multiple brain regions. After the signal delivery element(s) 104 have been deployed, an electrical signal can be applied to directly affect the neuronal cells at the target region.

Figure 2:
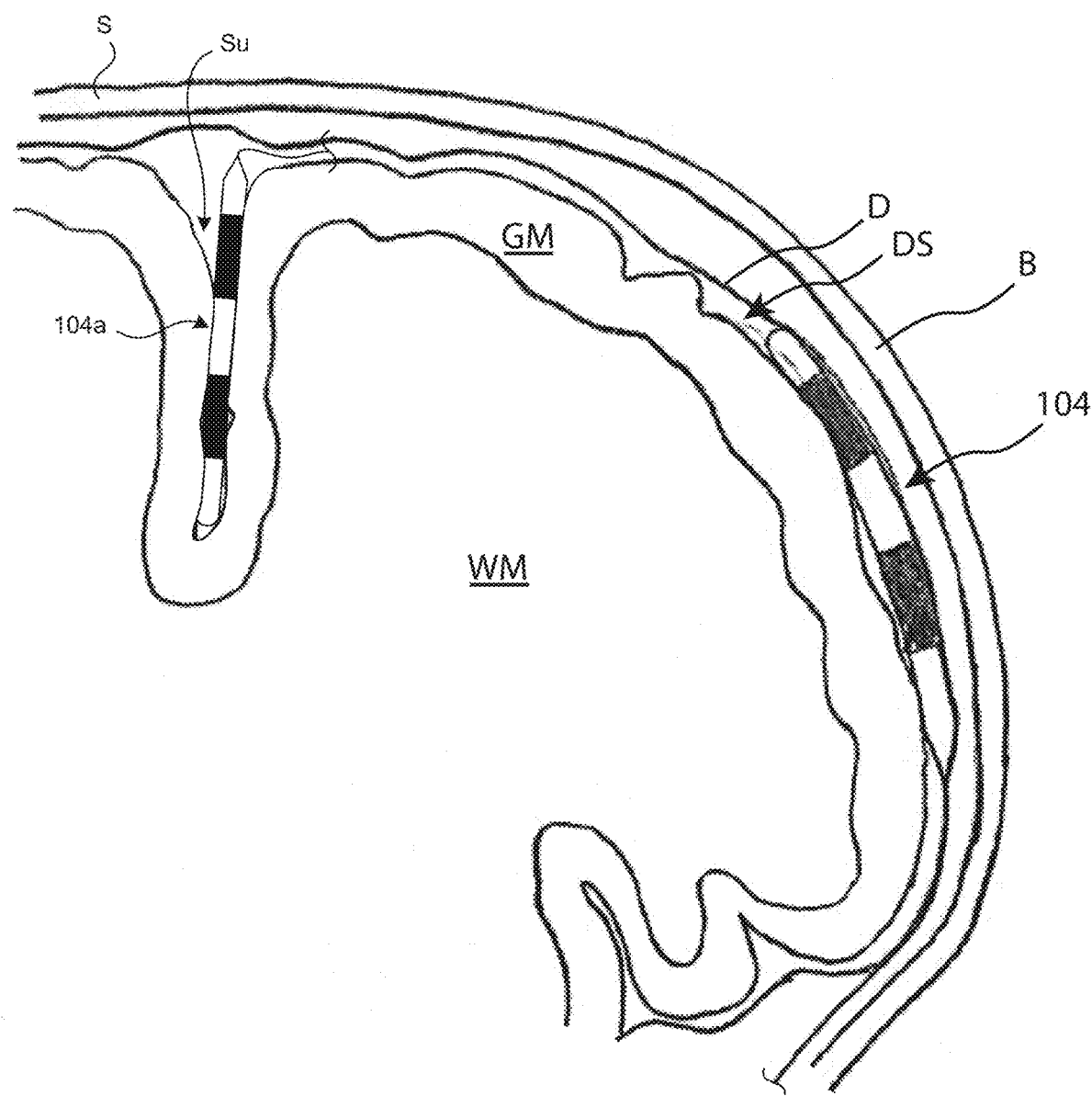
FIG. 2 is a partially schematic, cross-sectional illustration of a patient's brain, illustrating cortical implantation techniques, in accordance with some embodiments of the present technology.

FIG. 2 is a partially schematic, cross-sectional illustration of a representative signal delivery element(s) 104 placed at a cortical, rather than deep brain, location, in accordance with some embodiments of the present technology. In particular, the signal delivery element(s) 104 can be positioned within the patient's dura D, in the subdural space DS, so as to lie along or adjacent to the gray matter GM of the patient's cortex. In other embodiments, a signal delivery element(s) 104a can be placed within a sulcus S (e.g., the central sulcus Su) so as to better access neural populations within the folds of the patient's cortex. In still further embodiments, the signal delivery element(s) can be positioned epidurally. Any of the foregoing cortical approaches are generally less invasive than a deep brain approach. Conversely, the deep brain approach provides access (or closer access) to a greater selection of neural populations than a cortical approach. The approach chosen for a particular patient can therefore depend upon one or more variables, including the patient's condition, and the type of neural structures that are expected to best respond to the treatment, among other factors. In at least some embodiments, whether the electrical signal is applied to a cortical or deep brain location, an effect of the signal can be to target areas of the brain that may suffer from a dopamine deficit. The target area can be at a site of dopamine production, and/or at a site in a neural circuit that includes dopamine-producing areas.

Representative Signal Parameters

The electrical stimulation pulses delivered via the signal delivery element(s) 104 to a brain region of the patient can include a variety of waveforms. In some embodiments, the waveform can include a monophasic waveform, a charge balanced biphasic waveform, a charge imbalanced biphasic waveform and/or a charge balanced biphasic waveform with a delay (e.g., an interphasic delay between the cathodic phase and the anodic phase of the pulse). In some embodiments, it is believed that charge balanced biphasic waveforms at frequencies from 1.2 kHz to 500 KHz and with an interphasic delay can provide more efficacious neuromodulation, while also mitigating the risk of damaging adjacent tissue, when used to treat the brain region. It is believed that charge balanced biphasic waveforms with an interphasic delay can also allow for a distinct mechanism of action (e.g., quieting overly active neuronal cells) for treating the brain region of the patient, compared to other conventional brain stimulation techniques.

In any of the foregoing embodiments, aspects of the therapy provided to the patient may be varied within suitable ranges to produce beneficial results for patients suffering from motor and/or other disorders. For example, the location of the signal delivery (and in particular, the locations of active contacts or electrodes) can be varied by moving the signal delivery device and/or by selecting different electrodes or contacts carried by the signal delivery device. Other characteristics of the applied signal can also be varied. For example, the signal can be delivered at a frequency of from about 1.2 kHz to about 500 KHz, and in particular embodiments, from about 1.5 kHz to about 500 kHz, from about 1.2 kHz to about 250 kHz, from about 1.2 kHz to about 100 kHz, from about 1.2 kHz to about 50 kHz, or from about 1.2 kHz to about 25 KHz. In further particular embodiments, the signal can be provided at frequencies greater than 4 kHz or greater than 5 kHz, e.g., from about 5 kHz to about 20 kHz, or from about 5 kHz to about 15 kHz, or from about 5 kHz to about 10 KHz. In further embodiments, the frequency range can be or extend from 5 kHz, 6 KHz, 7 kHz, 8 KHz, 9 kHz or 10 KHz to any of 15 kHz, 30 kHz, 50 kHz, or 100 kHz. In further embodiments, and as described in more detail below, frequencies from about 1.2 kHz to about 500 KHz can be used in tandem with lower frequencies (below 1.2 kHz), such as frequencies less than about 1000 kHz, or less than about 250 Hz, or from about 10 Hz to about 150 Hz, or from about 60 Hz to about 130 Hz.

For the frequencies or frequency ranges disclosed above between 1.2 kHz and 500 kHz, the amplitude of the signal can range from about 0.1 mA to about 20 mA in some embodiments, and in some embodiments, can range from about 0.1 mA to about 15 mA, or about 0.1 mA to about 10 mA, or about 0.1 mA to about 7.5 mA, or about 0.1 mA to about 4 mA or about 0.5 mA to about 10 mA, or about 0.5 mA to about 4 mA, or about 4 mA to about 7 mA, or about 4 mA to about 10 mA, or about 2 mA to about 5 mA, or about 3.0 mA to about 5.0 mA, or about 2 mA to about 4 mA, or about 4 mA to about 6 mA, or about 0.5 mA to about 2.5 mA. In some embodiments, the amplitude of the signal may be selected based on a variety of factors including the mechanism of action, the target stimulation site (e.g., the STN or GPi), expected efficacy of the treatment, expected side effects, expected time for an electrical signal to take effect. In another example, a higher amplitude may be used during later phases of the treatment, e.g., if the patient's response to a lower amplitude signal begins to fade over time. As yet another example, the higher amplitude may be used when the signal is applied to a particular structure (e.g., the STN) known or expected to respond more favorably (e.g., to produce no or less undesirable side effects) to the higher amplitude. The lower amplitude may be used when the signal is applied to a particular structure (e.g., the GPi) known or expected to respond more favorably to the lower amplitude. In still another embodiment, a higher amplitude (e.g., an amplitude of about 5-7 mA) may be used when the signal is intended to cause a therapeutic effect by exciting/activating neural elements. In a related example, a lower amplitude (e.g., an amplitude of about 2-5 mA) may be used when the signal is intended to cause a therapeutic effect by inhibiting/suppressing neural elements.

An advantage of some embodiments of the present technology is that using the above-noted frequency ranges of about 1.2 kHz to about 500 KHz allows a physician, clinician, and/or other personnel to use a broader range of amplitudes, compared to when a lower frequency range of less than about 1200 Hz or 1000 Hz is used. This can be particularly beneficial because the amplitudes needed to treat a particular patient may change, continuously or otherwise over the course of time. For instance, in some patients the amplitude needs can increase over time, as indicated above. Accordingly, the expected increase in available amplitude range associated with treating the patient at the 1.2 kHz to 500 KHz frequency range can allow the patient to receive treatment over a longer period of time and/or with increased efficacy and/or decreased side effects.

The pulse width of the signal can vary over a suitable range from about 1 microsecond to about 400 microseconds. The particular maximum pulse width value selected is established by the frequency of the signal, by inter-phase intervals, and by the phase nature of the signal (monophasic or biphasic). Within the range capped by the maximum value, the pulse width can be selected based on neural response, reduction in side effects and/or other factors, such as energy consumption. Other signal parameters (e.g., frequency, duty cycle, amplitude, waveform, etc.) may also be selected based on the same variety of factors.

As used herein, the pulse width of the signal refers to just the cathodic phase of the pulses, or alternatively just the anodic phase. In further particular examples, the pulse width can vary from about 1 microsecond to about 333 microseconds. For example, in some embodiments, the pulse width can be about 2 microseconds, about 3 microseconds, or about 4 microseconds. In some embodiments, the pulse width can range from about 10 microseconds to about 333 microseconds, or from about 25 microseconds to about 166 microseconds, or from about 33 microseconds to about 100 microseconds, or from about 50 microseconds to about 166 microseconds, or from about 30 microseconds to about 35 microseconds. The pulses can be delivered in a biphasic manner (e.g., for charge balancing), with the anodic and anodic pulses symmetric or asymmetric. The specific values selected for the foregoing parameters may vary from patient to patient and/or from indication to indication and/or on the basis of the selected target neural population, and/or on the basis of the electrode location. In addition, the methodology may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values.

For any of the frequencies, frequency ranges, amplitude ranges, pulse width ranges, or combinations thereof, disclosed above, in some embodiments, the duty cycle may be varied e.g., to be less than 100%, or less than 75% or less than 50%. The lengths of the on/off periods for a given duty cycle can also be varied. For example, patients may have improved therapeutic effects (e.g., improved motor functioning) and decreased unwanted side effects (e.g., motor side effects, sensory side effects, and/or general side effects), any of which can persist for significant periods after the stimulation has been halted. Accordingly, the signal generator can be programmed to halt stimulation for periods of up to several seconds, minutes or hours, with appropriate allowances for the time necessary to re-start the beneficial effects. This arrangement can significantly reduce system power consumption, compared to systems with higher duty cycles, and compared to systems that have shorter off periods.

In addition to or in lieu of duty cycling, the therapy being delivered to a patient can vary between a first signal (e.g., at 1.2 kHz to 500 kHz) and a second signal having a lower frequency (e.g., less than 1200 Hz, or less than 1000 Hz, and in some embodiments, less than 130 Hz). The two signals can each be on for equal time durations or different time durations. For example, the first signal can be on for 10 seconds and can be followed by the second signal being on for 10 seconds, or the first signal can be on for 30 seconds and can be followed by the second signal being on for 10 seconds (or vice versa). The first signal and the second signal can be iteratively interleaved with one another throughout at least a portion of a therapy session.

It has been observed that patients can exhibit improved therapeutic effects (e.g., improved motor functioning) and decreased unwanted side effects (e.g., motor side effects, sensory side effects, and/or general side effects) that persist for periods of time after the first (e.g., higher frequency) therapy signal has halted and while the second (e.g., lower frequency) therapy signal is active. In some examples, the improved therapeutic effects can persist for 5-30 minutes, and up to several hours or even days. Accordingly, the signal generator can be programmed to transition between the first signal and the second signal for periods of up to several seconds, minutes or hours, with appropriate allowances for the time necessary to re-start the improved therapeutic effects (e.g., via the first signal). This arrangement can significantly reduce system power consumption, compared to systems with higher duty cycles and/or shorter off periods.

In view of the foregoing, the duty cycle of the overall signal may be varied, e.g., to be less than 100%, or less than 75%, or less than 50%, such that the signal being delivered to a patient can vary between the first signal, the second signal, and an off period. The first signal, second signal, and off period can each be in effect for equal time durations or different time durations, as described above. In some embodiments, the second signal can extend the improved benefits for a longer time period, compared to the time period during which benefits are extended when the signal is halted. Accordingly, the combination of the first signal, the second signal, and the off period can reduce (e.g., optimally reduce) power consumption, compared to systems with higher duty cycles and/or shorter off periods.

In any of the foregoing embodiments, the parameters in accordance with which the signal generator 102 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner.

Representative Methods

Figure 3:
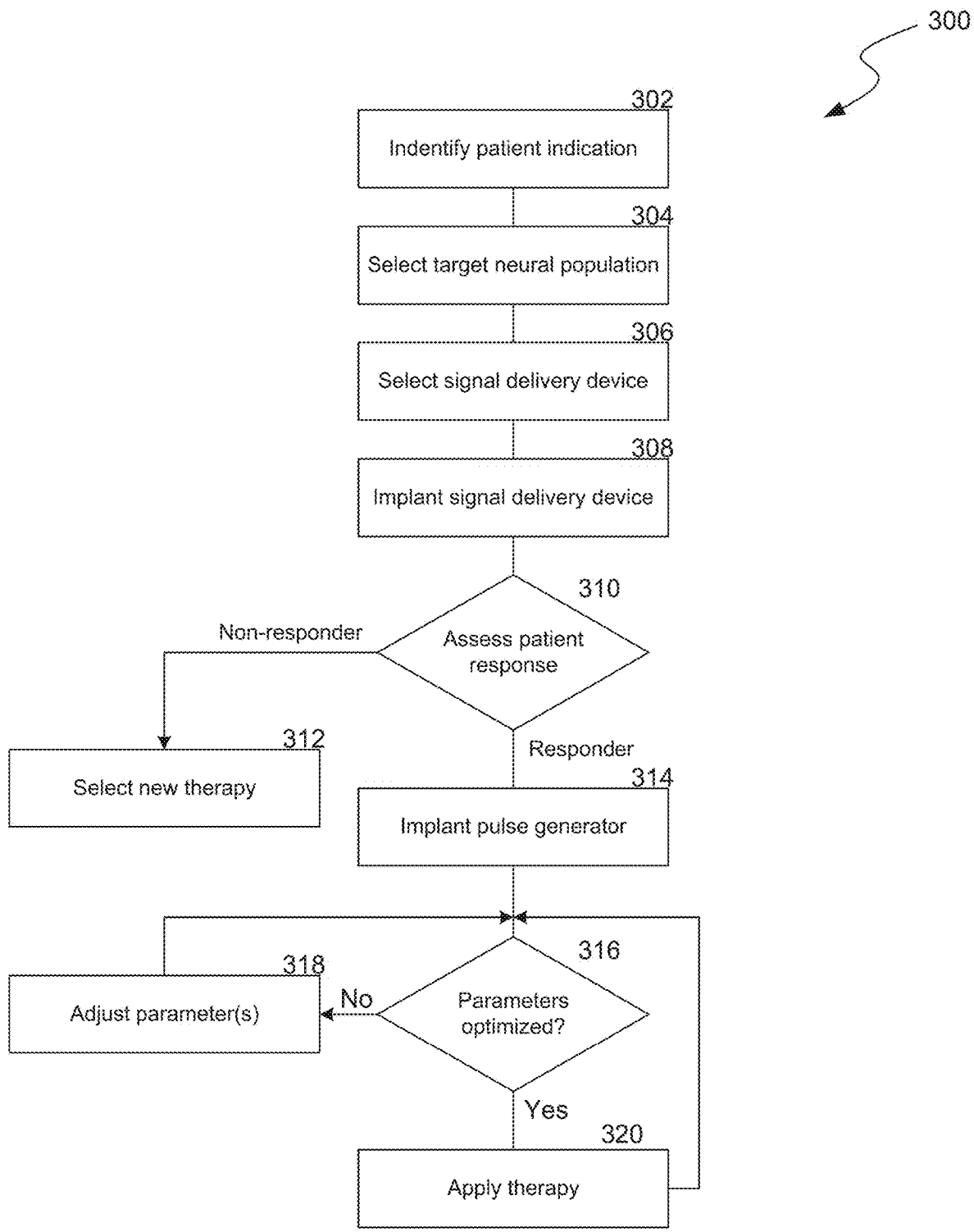
FIG. 3 is a flow diagram illustrating a representative process in accordance with some embodiments of the present technology.

FIG. 3 illustrates a process 300 for treating patients in accordance with some embodiments of the present technology. Some or all elements of the process can be conducted via machine-readable instructions that are contained on or in any suitable element or elements of the system (e.g., the implanted signal generator 102, the external signal generator 115, the physicians programmer or controller 118, and/or the patients programmer or controller 119, described above with reference to FIG. 1). Block 302 includes identifying a patient indication amenable to treatment via the techniques disclosed herein. Representative indications include tremor (e.g., essential tremor, stroke-induced tremor, and/or other tremors), and Parkinson's disease (which can include bradykinesia, akinesia, dyskinesia, tremor, rigidity, postural abnormalities, and/or gait abnormalities). In some embodiments, the indication can include other motor disorders, non-motor disorders, and/or other neurological conditions, depending upon the patient. For example, representative non-movement disorders can include sensory disorders, such as chronic pain. Other representative disorders include speech disorders, epilepsy, and neuropsychiatric disorders.

In block 304, the process includes selecting a target neural population. The selected neural population will depend at least in part upon the patient indication to be treated. In some embodiments, the target location can include the thalamus for example, and can include other suitable locations in other embodiments. In some cases, the patient's condition may be treated by modulating any of several different neural populations including those listed herein, with the target population selected based on factors that include its integrity or level of neural damage to the population, how accessible the neural population is, and/or the likelihood that the neural population will respond favorably to the therapy signal.

At block 306, the process includes selecting a signal delivery device. For example, the process can include selecting the signal delivery device to include a deep-brain probe, a cylindrical cortical lead, a cortical paddle lead, and/or another suitable device. The device selected for a particular patient will depend on a number of factors, including which target neural population is selected at block 304, the patient's condition (e.g., the patient's tolerance for invasive procedures), and/or other factors.

At block 308, the signal delivery device is implanted so that the contacts, electrodes, and/or other elements that deliver the electrical therapy signal to the target neural population, are properly positioned. In some embodiments, during an initial phase (e.g., the trial period) of the process following the signal delivery device implant, the patient can receive therapeutic signals via an external signal generator, as described above with reference to FIG. 1. During this phase, the patient can be assessed for responsive behavior (block 310). If the patient is a "non-responder" the process can include selecting a new therapy for the patient (block 312). If the patient is a "responder", the process can include implanting a signal generator (block 314) and connecting the implanted signal generator to the signal delivery device implanted at block 308, or to a newly implanted signal delivery device. Or, as was also discussed above with reference to FIG. 1, the practitioner can implant a signal generator without first using an external pulse generator. Whether or not the patient undergoes a trial period with an external signal generator, the implanted signal generator can be implanted at a subclavicular location as discussed above with reference to FIG. 1, or at other suitable locations. Such locations can include a cranial location (e.g., with the implanted signal generator implanted beneath the scalp, but external to the skull, or within the skull), or a cochlear location. In any of these examples, the signal generator can be shaped and sized to allow implantation at the desired location. As battery and electronic circuitry technologies continue to evolve, it is expected that the signal generators can be made smaller, thus increasing the selection of sites suitable for implantation.

At block 316, the process can include determining whether the modulation parameters with which the therapy signal is delivered are optimized, or at least improved, compared to a suitable baseline (e.g., the patient's initial condition). If not, then at block 318 the parameters are adjusted and the patient's response reassessed. If the parameters are optimized, then the process can include continuing to apply the therapy via the implanted pulse generator (block 320).

In some embodiments, the process can return to block 316 to determine whether the parameters are, or remain, optimized. This loop can be based on the passage of time, and/or other factors. For example, the parameters can be assessed at regular intervals, measured on a scale of seconds, minutes, hours, days or weeks. In addition to or in lieu of a time-based feedback process, the process can respond to information corresponding more directly to the efficacy of the patient's therapy. For example, if the patient has been suffering from a tremor, and an accelerometer indicates that the initially suppressed tremor has reappeared, then the process can return to blocks 316 and 318 to adjust the parameters for improved therapeutic efficacy. In some embodiments, the feedback loop can respond to inputs other than accelerometer inputs, e.g., as described above with reference to FIG. 1. In some embodiments, other feedback mechanisms can include receiving electrophysiological signals from the brain, for example the subthalamic nucleus (STN) and, based upon the feedback, change signal delivery parameters such as an amplitude, frequency and/or pulse width.

Figure 4A:
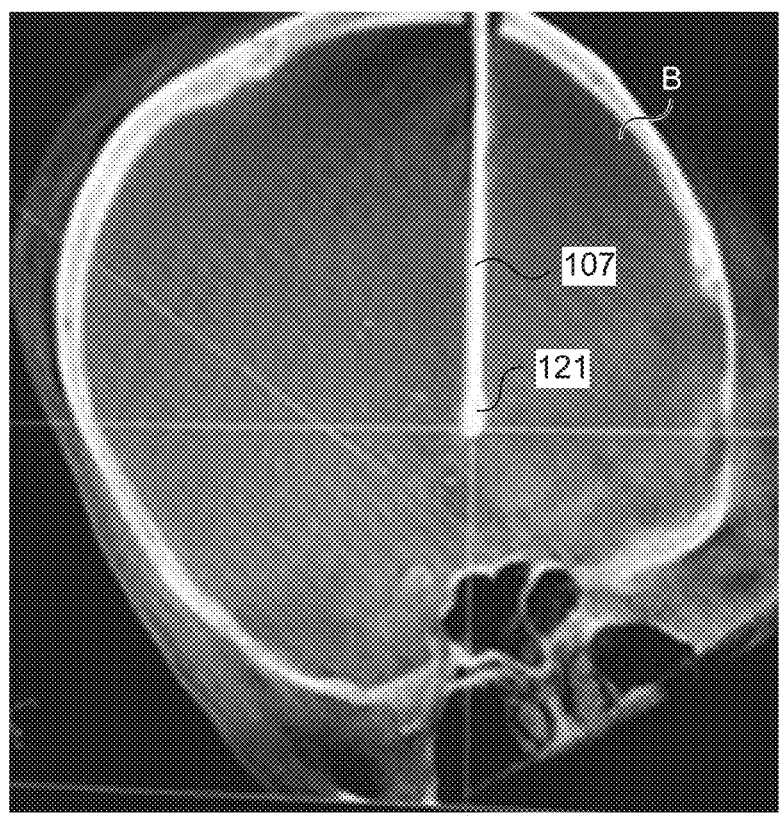
FIGS. 4A-4B illustrate a deep brain probe implanted in a patient, in accordance with some embodiments of the present technology.
Figure 4B:
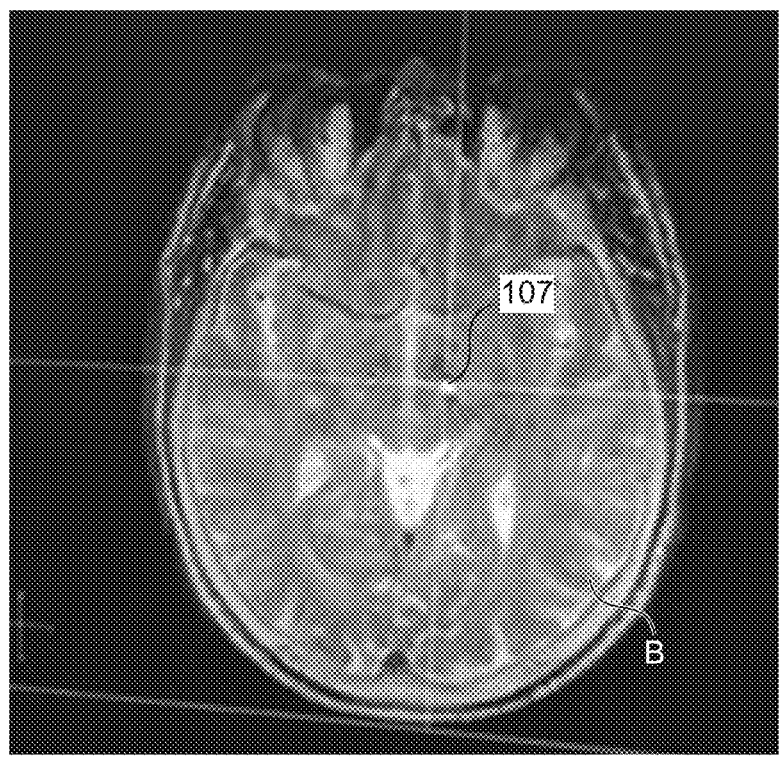

FIGS. 4A and 4B illustrate a representative lead or probe 107 implanted in a representative patient's brain B in accordance with some embodiments of the present technology. FIG. 4A is an image taken in the plane of the probe 107, indicating that a tip 121 of the probe 107 is located at the subthalamic nucleus (STN) of the patient's brain. FIG. 4B is an end-on view of the probe 107 shown in FIG. 4A.

After the patient was implanted with the probe 107 at the location shown in FIGS. 4A and 4B, a therapy signal was directed to the probe 107 at a frequency of about 10 KHz, a pulse width of 30 microseconds, and an average amplitude of about 4 mA. The patient, who was suffering from uncontrolled hand tremors, responded nearly immediately to the modulation signal, with the tremors ceasing. When the therapy signal was discontinued (during the course of a short, intraoperative procedure), the tremor returned. The intraoperative process (which included accounting for insertion effects, described above) was sufficient to determine that the patient qualified as a responder, and so the patient received an implant, in accordance with the process described above with reference to FIG. 3.

During a typical intraoperative procedure, the patient can be evaluated on the basis of one or more suitable parameters, including for example, head tremor, face tremor, voice tremor, and/or upper extremity tremor, rigidity, akinesia, dyskinesia, speech impairment, etc. The upper extremity tremor can be evaluated as the patient performs multiple tasks. Representative tasks include moving the right upper extremity forward, moving the right upper extremity to a wing position, moving the left upper extremity to a wing position, moving the right upper extremity kinetically, and/or moving the left upper extremity kinetically. The patient's lower extremity tremor, Archimedes spiral tremor, hand writing, performance on a dot approximation task, and/or other tasks can also be evaluated during the intraoperative process.

As described above, an expected advantage of embodiments of the present technology (based at least in part on a clinical comparison of patients who received intraoperative conventional therapy at a frequency of 130 Hz, and patients who received intraoperative therapy at a frequency of 10 kHz) is that the side effects experienced by the patient will be reduced compared to those associated with conventional brain stimulation techniques. Such side effects can manifest as motor side effects, sensory side effects, and/or general side effects. Typical motor side effects that are expected to be reduced or eliminated include twitching effects and dysarthria. Typical sensory side effects that are expected to be reduced or eliminated including dysesthesia and/or paresthesia, hypoesthesia, adverse effects on temperature sensation, and/or pain. For example, many patients receiving traditional deep brain stimulation perceive paresthesia in the face, arms, or other areas of the body. It is expected that therapy in accordance with the parameters described herein can produce effective results, without such side effects.

The presently disclosed therapy can also reduce or eliminate more general side effects while maintaining or improving typical therapy. Typical general side effects expected to be reduced or eliminated include blurring sensations, light-headedness, dizziness, vision changes and/or mood changes and alterations. Further representative side effects that may be reduced or eliminated include deficient neurotransmitter concentrations (e.g., for dopamine and/or other neurotransmitters). Additional side effects that may be avoided or reduced via treatment in accordance with embodiments of the present technology include adversely affecting the patient's speech, gait, expressions, balance, memory, emotions and/or cognitive abilities, in addition to or in lieu of the motor effects described above. Representative cognitive processes that are not expected to be affected by the foregoing therapy techniques include forming thoughts, and/or selecting thoughts from multiple possible thoughts in an organized rather than confused manner. In addition, the present therapy is not expected to contribute negatively to anxiety, depression, addictions, and/or emotional disorders in the patient. In fact, in some embodiments it is expected that emotional disorders, anxiety, depression, addiction, and the emotions resulting from these conditions can be reduced, for example when the target location is at or near the habenula. These effects can be particularly significant because more traditional or conventional brain stimulation (e.g., at frequencies less than 1200 Hz) can result in many of the above-identified side effects. These lower frequencies, when used without interleaving higher frequency signals, can worsen a patient's speech and over time cause further speech-related issues. Accordingly, one of the benefits of embodiments of the present technology using higher frequencies (e.g., 1.2 kHz to about 500 kHz) is that the technology can improve or at least not worsen the patient's pre-existing speech deficit.

The foregoing example describes an instance in which the therapy is used to treat a disorder or dysfunction without causing or worsening a side effect (e.g., a speech deficit). In still further embodiments, what is considered a side effect of treating a disorder may itself be a disorder and/or a symptom of a disorder. For example, a patient may have a disorder that is or includes a speech deficit. Embodiments of the present technology can be used to directly treat the speech deficit, by applying a therapy signal having parameters as described herein. This is in direct contrast to the typical patient experience with devices administering therapy signals at a frequency of less than 1.2 KHz. Such experiences can include deliberately turning the device off before speaking in order to avoid the speech impediments created by the therapy signal. Instead, embodiments of the present technology can use a frequency signal of 1.2 kHz or above to improve, rather than exacerbate, the patient's speech deficit.

Still further, in at least some conventional treatment modalities (e.g., using an electrical therapy signal with a frequency of less than 1.2 kHz), improving one symptom and/or side effect results in create or worsening another symptom and/or side effect. By contrast, it is believed that therapies applied accordance with embodiments of the present technology can result in improving at least one symptom and/or side effect without creating or worsening another symptom and/or side effect.

As discussed above, an expected advantage of embodiments of the present technology, when compared to traditional or conventional brain stimulation techniques (e.g., at frequencies less than 1200 Hz or less than 1000 Hz), is that the present technology can allow a physician or operator to use a broader range of amplitudes for stimulation. This same benefit holds true for side effects, as the amplitude window within which detrimental side effects are inhibited, or at least not exaggerated, is greater when higher frequency stimulation (as disclosed herein), is used, compared to when lower frequency stimulation of conventional technologies is used.

As discussed above, another expected advantage of embodiments of the present technology, when compared to traditional or conventional brain stimulation techniques, is that the present technology can produce greater efficacy. For example, treatment in accordance with embodiments of the present technology provided an increased effectiveness to improve a patient's speech and/or rigidity symptoms, compared to conventional brain stimulation techniques. Without being bound by theory, the increased efficacy may be attributed to a possible mechanism of action by which embodiments of the present therapy operate, which is to quiet overly active neuronal cells.

In addition to producing greater efficacy, therapy signals in accordance with the present technology may allow the practitioner to treat motor and/or other dysfunctions by targeting brain structures that are not typically targeted using conventional therapies. For example, traditional deep brain stimulation typically is not directed to the hippocampus, so as to avoid unintended detrimental effects on the patient's memory. The present therapy may avoid such detrimental effects and therefore may provide one or more additional options for patient treatment.

More generally, embodiments of the present technology are directed to providing an effective therapy to a patient via an electrical therapy signal, without the signal generating non-therapeutic (e.g., undesirable) side effects, or generating such side effects, but at a reduced level compared with the side effects associated with electrical stimulation at frequencies below 1.2 kHz. What constitutes an "effective therapy" typically varies from indication to indication, but in many instances, has a value that is commonly accepted by practitioners in the field. For example, for Parkinson's disease, the Unified Parkinson's Disease Rating Scale is used to measure the patient's condition, and a decrease of at least 30% on Part 3 of the scale is considered an effective therapy. For psychiatric disorders, the Hamilton Depression Rating is used, and a reduction of 50% is generally considered to be effective therapy. The foregoing are two representative examples, and FIG. 5 provides further representative examples, along with target locations at which the therapy may be delivered, and representative side effects that are reduced or eliminated via therapy in accordance with the present technology. The side effects do not include an "onset response," which is a brief sensory response typically experienced by patients at the beginning of a therapy treatment. While the examples provided herein indicate representative efficacy measures, and representative side effects, the technology need not be specifically limited thereby, unless noted.

Certain aspects of the present technology described in the various embodiments above may be simplified, modified, combined or eliminated in other embodiments. For example, features described under any of the headings above may be combined with features described under other headings. Therapies directed to addressing particular indications may be combined. The thalamus, or structures within the thalamus, may be targeted for addressing motor dysfunctions, as described above. In some embodiments, the thalamus may be targeted for addressing sensory defects, including chronic pain. Because the thalamus includes centers for sensing pain, touch, hot, cold, and texture, applying deep brain stimulation to the thalamus may address defects associated with any of the foregoing senses, including chronic pain indications. Further, while advantages associated with certain embodiments have been described in the context of those embodiments, other embodiments may also exhibit such advantages, and not all embodiments need necessarily exhibit such advantages to fall within the scope of the present disclosure.

To the extent any materials incorporated herein by reference conflict with the present disclosure, the present disclosure controls. As used herein, the term "and/or", as in "A and/or B" covers A alone, B alone, and both A and B. As used herein, the term "about" refers to a value within a range of +10% of the identified value, unless otherwise noted.

The following examples provide further representative embodiments of the presently disclosed technology.
 1. A method for treating a patient, comprising: applying a therapy signal to a patient, via at least one electrode at a subdural or epidural location at the patient's brain, to provide effective therapy that reduces or eliminates effects of a patient disorder, without the therapy signal inducing any non-therapeutic side effects, wherein the therapy signal has a frequency in a frequency range from 1.2 kHz to 500 KHz, an amplitude in an amplitude range from 0.1 to 20 mA, and a pulse width in a pulse width range from 1 microsecond to 400 microseconds.
 2. A method for treating a patient, comprising: programming a signal generator to apply a therapy signal to a patient, via at least one electrode at a subdural or epidural location of the patient's brain, to provide effective therapy that reduces or eliminates effects of a patient disorder, without the therapy signal inducing any non-therapeutic side effects, wherein the therapy signal has a frequency in a frequency range from 1.2 kHz to 500 KHz, an amplitude in an amplitude range from 0.1 to 20 mA, and a pulse width in a pulse width range from 1 microsecond to 400 microseconds.
 3. A system for treating a patient, comprising: an signal delivery device configured to be implanted at a subdural or epidural location of the patient's brain, and an implantable pulse generator, coupleable to the signal delivery device and programmed with instructions that, when executed direct a therapy signal to a patient, via the signal delivery device, to provide effective therapy that reduces or eliminates effects of a patient disorder, without the therapy signal inducing any non-therapeutic side effects, wherein the therapy signal has a frequency in a frequency range from 1.2 kHz to 500 kHz, an amplitude in an amplitude range from 0.1 to 20 mA, and a pulse width in a pulse width range from 1 microsecond to 400 microseconds.

We claim:

1. A method for treating a patient, comprising:
applying a therapy signal to a target neural population in a patient's brain, via at least one electrode positioned at the patient's globus pallidus internus (GPi), to reduce or eliminate effects of a patient disorder, without the therapy signal inducing paresthesia, wherein the therapy signal has a frequency in a frequency range from 5 kHz to 100 kHz, an amplitude in an amplitude range from 0.1 mA to 20 mA, and a pulse width in a pulse width range from 10 microseconds to 333 microseconds.

2. The method of claim 1 wherein the patient disorder includes at least one of: a motor disorder, a sensory disorder or a neuropsychiatric disorder.

3. The method of claim 1 wherein the therapy signal does not induce any sensory side effects, cognitive side effects or motor side effects.

4. The method of claim 3 wherein:
the motor side effects include at least one of twitching or dysarthria,
the sensory side effects include at least one of dysesthesia, hypoesthesia, adverse effects on temperature sensation, or pain, and
the cognitive side effects include adversely affecting at least one of forming thoughts, selecting thoughts from multiple possible thoughts in an organized manner, or initiating motor actions.

5. The method of claim 1 wherein the patient disorder includes Parkinson's disease, and wherein the therapy signal does not impede speech.

6. The method of claim 1 wherein the frequency is at least 50 KHz.

7. The method of claim 1 wherein the amplitude is from 0.1 mA to 10 mA.

8. The method of claim 1 wherein the pulse width is in a pulse width range from 30 microseconds to 35 microseconds.

9. A method for treating a patient, comprising:
applying a therapy signal to a target neural population in a patient's brain, via at least one electrode positioned at the patient's globus pallidus internus (GPi), to reduce or eliminate effects of a patient disorder, without the therapy signal inducing any of the following non-therapeutic side effects: paresthesia, interference with motor activity, and interference with cognitive activity; and
wherein the therapy signal has a frequency in a frequency range from 5 kHz to 100 kHz, an amplitude in an amplitude range from 0.1 mA to 20 mA, and a pulse width in a pulse width range from 10 microseconds to 333 microseconds.

10. The method of claim 9 wherein the patient disorder includes at least one of: a motor disorder, a sensory disorder or a neuropsychiatric disorder.

11. The method of claim 9 wherein the side effects include at least one of twitching or dysarthria.

12. The method of claim 9 wherein the side effects include adversely affecting at least one of forming thoughts, selecting thoughts from multiple possible thoughts in an organized manner, or initiating motor actions.

13. The method of claim 9 wherein the frequency is at least 50 KHz.

14. The method of claim 9 wherein the amplitude is from 0.1 to 4 mA.

15. The method of claim 9 wherein the pulse width is in a pulse width range from 30 microseconds to 35 microseconds.

16. A method for treating a patient, comprising:
applying a therapy signal to a target neural population in a patient's brain, via at least one electrode positioned at the patient's globus pallidus internus (GPi), to reduce or eliminate effects of a patient disorder, wherein the therapy signal has a frequency in a frequency range from 5 kHz to 100 kHz, an amplitude in an amplitude range from 0.1 mA to 20 mA, and a pulse width in a pulse width range from 10 microseconds to 333 microseconds, and wherein the therapy signal induces fewer non-therapeutic side effects in the patient than a therapy signal having a frequency of less than 1.2 KHz.

17. The method of claim 16 wherein the patient disorder includes at least one of: a motor disorder, a sensory disorder or a neuropsychiatric disorder.

18. The method of claim 16 wherein the side effects include at least one of: sensory side effects, cognitive side effects or motor side effects.

19. The method of claim 18 wherein:
the motor side effects include at least one of twitching or dysarthria,
the sensory side effects include at least one of dysesthesia, paresthesia, hypoesthesia, adverse effects on temperature sensation, or pain, and
the cognitive side effects include adversely affecting at least one of forming thoughts, selecting thoughts from multiple possible thoughts in an organized manner, or initiating motor actions.

20. The method of claim 16 wherein the patient disorder includes Parkinson's disease, and wherein the non-therapeutic side effect includes any speech impediment.

21. The method of claim 16 wherein the side effects include at least one of blurring sensations, light-headedness, dizziness, vision changes, mood changes or mood alterations.

22. The method of claim 16 wherein the frequency is at least 50 kHz.

23. The method of claim 16 wherein the amplitude is from 0.1 mA to 7 mA.

24. The method of claim 16 wherein the pulse width is in a pulse width range from 30 microseconds to 35 microseconds.

25. A method for treating a patient, comprising:
implanting at least one electrode at the patient's globus pallidus internus (GPi);
reducing or eliminating effects of a speech disorder of the patient without interfering with normal patient movement, sensations, or both, by applying a therapy signal to a target neural population of the patient's brain via the at least one electrode implanted at the patient's GPi, the therapy signal having a frequency in a frequency range of 5 kHz to 100 kHz, an amplitude in an amplitude range of from 0.1 mA to 20 mA, and a pulse width in a pulse width range of from 10 microseconds to 333 microseconds.

26. A method for treating a patient, comprising:
applying a therapy signal to a target neural population in a patient's brain, via at least one electrode positioned at the patient's globus pallidus internus (GPi), to reduce or eliminate effects of a patient disorder, without the therapy signal impeding speech, wherein the therapy signal has a frequency in a frequency range from 5 kHz to 100 kHz, an amplitude in an amplitude range from 0.1 mA to 20 mA, and a pulse width in a pulse width range from 10 microsecond to 333 microseconds.

27. A method for treating a patient, comprising:
applying a therapy signal to a target neural population in a patient's brain, via at least one electrode positioned at the patient's globus pallidus internus (GPi), to reduce or eliminate effects of a patient disorder, without the therapy signal worsening an emotional disorder and/or without the therapy signal impairing cognitive function, wherein the therapy signal has a frequency in a frequency range from 5 KHz to 100 kHz, an amplitude in an amplitude range from 0.1 mA to 20 mA, and a pulse width in a pulse width range from 10 microseconds to 333 microseconds.

28. The method of claim 27 wherein the therapy signal does not impair cognitive function, including impairing the patient's ability to form thoughts and/or to select thoughts from multiple possible thoughts in an organized manner.

29. The method of claim 27 wherein the therapy signal does not worsen the emotional disorder, and wherein the emotional disorder includes anxiety, depression, and/or addiction.

* * * * *

UNITED STATES PATENT AND TRADEMARK OFFICE
CERTIFICATE OF CORRECTION

PATENT NO. : 12,102,820 B1
APPLICATION NO. : 17/967805
DATED : October 1, 2024
INVENTOR(S) : Satinderpall Singh Pannu et al.

It is certified that error appears in the above-identified patent and that said Letters Patent is hereby corrected as shown below:

On the Title Page

On the page 2, in Column 2, under "Other Publications", Line 11, delete "hte" and insert -- the --.

In the Specification

In Column 8, Line 37, delete "KHz" and insert -- kHz --.

In Column 8, Line 56, delete "KHz," and insert -- kHz, --.

In Column 8, Line 60, delete "KHz." and insert -- kHz. --.

In Column 8, Line 64, delete "KHz." and insert -- kHz. --.

In Column 8, Line 66, delete "KHz," and insert -- kHz, --.

In Column 8, Line 66, delete "8 KHz," and insert -- 8 kHz, --.

In Column 8, Line 66, delete "KHz" and insert -- kHz --.

In Column 9, Line 2, delete "KHz" and insert -- kHz --.

In Column 9, Line 41, delete "KHz" and insert -- kHz --.

In Column 9, Line 51, delete "KHz" and insert -- kHz --.

In Column 14, Line 28, delete "KHz." and insert -- kHz. --.

In Column 16, Line 4, delete "KHz," and insert -- kHz, --.

Signed and Sealed this
Tenth Day of December, 2024

Katherine Kelly Vidal
*Director of the United States Patent and Trademark Office*

In Column 16, Line 15, delete "KHz," and insert -- kHz, --.

In the Claims

In Column 16, Line 65, in Claim 6, delete "KHz." and insert -- kHz. --.

In Column 17, Line 28, in Claim 13, delete "KHz." and insert -- kHz. --.

In Column 17, Line 45, in Claim 16, delete "KHz." and insert -- kHz. --.

In Column 18, Line 48, in Claim 27, delete "KHz" and insert -- kHz --.